(12) United States Patent
Takashi et al.

(10) Patent No.: US 8,721,333 B2
(45) Date of Patent: May 13, 2014

(54) AIR-DRIVEN ROTARY CUTTING TOOL

(75) Inventors: Tetsuya Takashi, Kyoto (JP); Shozo Nakayama, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 659 days.

(21) Appl. No.: 12/925,390

(22) Filed: Oct. 20, 2010

(65) Prior Publication Data
US 2011/0104636 A1 May 5, 2011

(30) Foreign Application Priority Data

Oct. 30, 2009 (JP) ................................. 2009-249983

(51) Int. Cl.
*A61C 1/05* (2006.01)
(52) U.S. Cl.
USPC .......................................... 433/132; 415/904
(58) Field of Classification Search
USPC ................. 433/132; 415/904, 202, 198.1, 222
See application file for complete search history.

(56) References Cited

U.S. PATENT DOCUMENTS

2001/0002975 A1 * 6/2001 Hashimoto et al. ........... 415/202

FOREIGN PATENT DOCUMENTS

| JP | 3208345 | 9/2001 |
| JP | 3672781 | 7/2005 |
| JP | 4160319 | 10/2008 |
| WO | WO 2006/101133 | 9/2006 |

* cited by examiner

*Primary Examiner* — Heidi M Eide
(74) *Attorney, Agent, or Firm* — DLA Piper LLP (US)

(57) ABSTRACT

An air-driven rotary cutting tool including a grip part, a head part provided at a distal end of the grip portion, and a rotor of double-wheel type rotatably installed in a hollow portion formed in the head part. The rotor has a first turbine blade portion provided with a plurality of first turbine vanes surrounding the rotary axis and a second turbine blade portion integrally formed with the first turbine blade and having a plurality of second turbine vanes surrounding the rotary axis. The first turbine vane has, on its side when seen in a direction into the rotary axis, a concave shape concaved in a direction of rotation of the rotor, and the second turbine vane has, on its side, a concave shape concaving in a direction opposite from the first turbine vane.

12 Claims, 8 Drawing Sheets

AIR-DRIVEN ROTARY CUTTING TOOL

TECHNICAL FIELD

The present invention relates to an air-driven rotary cutting tool for rotating a cutting tool utilizing a pressurized air for medical use, dental use or other cutting procedures and more specifically, for example, to an air turbine handpiece for dental use.

BACKGROUND ART

The Patent Citations 1 to 4 which have been proposed by the present applicant disclose an air-driven rotary cutting tool for medical use, dental use or other cutting procedures. The air-driven rotary cutting tool disclosed in these citations has a double-wheel rotor as a means for effectively converting the energy of a pressurized air to a rotating force. The double-wheel rotor has a ring-like hub, a first turbine blade part and a second turbine blade portion formed at the outer circumference of the hub. The first turbine blade portion has a plurality of first turbine vanes and the second turbine blade portion has a plurality of second turbine vanes, the vanes extending radially from the center of the hub.

The air-driven rotary cutting tool disclosed in the Patent Citations 1 to 4 has a grip part to be held by an operator and a head part provided at the tip end of the grip part, and it is formed like a handpiece. The head is formed with a hollow portion, a tubular inner housing which has an outer shape corresponding to the inner shape of the hollow portion is contained in the hollow portion, and the rotor and a bearing mechanism for rotatably supporting the rotor are contained in the inner housing. The rotor is designed so as to be detachable to each cutting tool along the axial center. The head part and the inner housing are provided with an air supply passage for emitting a pressurized air into the first turbine blade portion of the rotor and an exhaust passage for discharging the air supplied from the second turbine blade portion. The inner housing is provided with a connecting channel (guide part) for guiding the pressurized air from the first turbine blade portion to the second turbine blade portion. The pressurized air emitted from the air supply passage impinges the first turbine vane of the first turbine blade portion to rotate the rotor around the rotary axis. Then, the pressurized air is sent to the second turbine blade portion from the connecting passage and impinges the second turbine vane to further promote rotation of the rotor around the rotary axis. Thereafter, the pressurized air is discharged through the exhaust passage.

Thus according to the handpiece with the double-wheel rotor allows the energy of the pressurized air to be used most effectively at two turbine blade portions, thereby resulting in that the cutting tool can be rotated with a high torque feature under a high rotational speed comparing to the conventional handpiece.

PRIOR ART CITATION

Patent Citation

PATENT CITATION 1: Japanese Patent No. 3208345
PATENT CITATION 2: Japanese Patent No. 3672781
PATENT CITATION 3: PCT publication No. WO2006/101133A1
PATENT CITATION 4: Japanese Patent No. 4160319

DISCLOSURE OF INVENTION

Technical Problem

The handpiece for dental use executes medical treatment like cutting of teeth by inserting the head part of the handpiece into the oral cavity of a patient, therefore it is desired to be small so as to alleviate a feeling of discomfort of a patient and to enhance handling ability without blocking an operator's view. It can be thought that the diameter of the rotor is reduced in order to downsize the head part, however, rotation of the rotor is required to be heighten if a predetermined torque is to be obtained with a small rotor diameter. However, the durable rotational speed of the cutting tool to be fitted to the rotor is limited (the rotational number is equal to or less than 450,000 rpm in case of general dental cutting tool). When the rotational speed of the cutting tool is too high, there may cause a trouble such that the cutting tool is folded down to be damaged, the cutting tool may be projected out of the holder, or the noise and heat generation during cutting may be enlarged. Therefore, it has been difficult to downsize the head part without enlarging the rotational speed of the rotor.

The Patent Citation 2 discloses a handpiece applied with a double-wheel rotor in which a second air channel for guiding the air from the first turbine blade portion to a second turbine blade portion is formed with a single member and the area formed with the second air channel is larger than the area formed with an air supply passage, thereby preventing leakage of a pressurized air and slightly reducing the rotational speed of the rotor while keeping high torque. However, the rotational speed of the rotor obtained herein is not enough to sweep away the above-mentioned problems. Therefore effective reduction of the rotational speed of the rotor while keeping the torque has been required. The handpiece shown in this citation is designed to contain and support the rotor and the like via an air guide ring in the head part and the air guide ring has been one of factors to have difficulty in further downsizing of the head.

The present invention is proposed in view of the above-mentioned problems and has an object to provide an air-driven rotary cutting tool which can reduce the rotational speed of the rotor while keeping the rotary torque of the rotor and which can further downsize the head.

Technical Solution

According to the first present invention, an air-driven rotary cutting tool comprises a grip part adapted to be held by an operator, a head part provided at a distal end of the grip part, and a rotor rotatably supported to a hollow portion formed in the head part around its rotary axis with a bearing. The rotor comprises a first turbine blade portion provided with a plurality of first turbine vanes surrounding the rotary axis and a second turbine blade portion integrally formed with the first turbine blade portion and having a plurality of second turbine vanes surrounding the rotary axis. The head part comprises in the hollow portion an air supply port for emitting air into the first turbine blade portion of the rotor from an air supply passage provided at the grip part, a guide portion for guiding air from the first turbine blade portion into the second turbine blade portion, and an exhaust port for exhausting air from the second turbine blade portion to an exhaust passage provided at the grip part. Air emitted from the air supply port activates the first turbine blade portion from a substantially perpendicular direction relative to the rotary axis of the rotor to rotate the rotor around an axial center of the rotary axis and is exhausted from the first turbine blade portion along an axial direction of the rotary axis via a first air channel provided between the first turbine vanes, then is guided by the second turbine blade portion through a second air channel provided at the guide portion, whereas air guided into the second turbine blade portion activates the second turbine blade portion in direction substantially perpendicular to the rotary axis to impel rotation of the rotor, then is exhausted from the exhaust port through a third air channel provided between the second turbine vanes. The present invention is characterized in that the first turbine vane has such a concave shape on its side seen in a direction into the rotary axis as to fall from upstream into downstream of its rotational direction of the rotor, while the second turbine vane has such a concave shape on its side as to fall into its opposite direction of the first turbine vane.

In this invention, it is desirable that the second air channel comprises a plurality of concave spaces defined by a plurality of wall portions formed inner circumference of the hollow portion of the head part and parallel to the rotary axis and a bottom wall portion formed between the wall portions and across faces parallel to the rotary axis, and each of the concave spaces is defined by a first face constituting a surface of the bottom wall portion, a second face comprised of a curved surface continuously erecting from a centrifugal side relative to the rotary axis of the first face, and a third face and a fourth face constituting an inner surface on the bottom wall portion side of the wall portions disposed at both sides of the bottom wall portion.

In this case, the bottom wall portion may be provided so as to orient toward a radiation direction from its axial center of the rotary axis or may be provided slanted so as to be apart toward downstream side of its rotational direction of the rotor relative to the radiation direction from the axial center of the rotary axis. In addition, connecting portions of the first and second faces and the third and fourth faces are preferably formed continuously with a curved surface. Further, in the third and fourth faces, the third face provided at upstream of its rotational direction of the rotor is desirably formed with a fifth face slanted toward the bottom wall portion by being cut out the opening side of the concave space.

According to the second present invention, an air-driven rotary cutting tool comprises a grip part adapted to be held by an operator, a head part provided at a distal end of the grip part, and a rotor rotatably supported to a hollow portion formed in the head part around its rotary axis with a bearing. The rotor comprises a first turbine blade portion provided with a plurality of first turbine vanes surrounding the rotary axis and a second turbine blade portion integrally formed with the first turbine blade portion and having a plurality of second turbine vanes surrounding the rotary axis. The head part comprises in the hollow portion an air supply port for emitting air into the first turbine blade portion of the rotor from an air supply passage provided at the grip part, a guide portion for guiding air from the first turbine blade portion into the second turbine blade portion, and an exhaust portion for exhausting air from the second turbine blade portion to an exhaust passage provided at the grip part. The air emitted from the air supply port activates the first turbine blade portion from a substantially perpendicular direction relative to the rotary axis of the rotor to rotate the rotor around an axial center of the rotary axis and is exhausted from the first turbine blade portion along an axial direction of the rotary axis via a first air channel provided between the first turbine vanes, then is guided by the second turbine blade portion through a second air channel provided at the guide portion, whereas air guided into the second turbine blade portion activates the second turbine blade portion in direction substantially perpendicular to the rotary axis to impel rotation of the rotor, then is exhausted from the exhaust port through a third air channel provided between the second turbine vanes. The present invention is characterized in that the second air channel comprises a plurality of concave spaces defined by a plurality of wall portions formed inner circumference of the hollow portion of the head part and parallel to the rotary axis and a bottom wall portion formed between the wall portions and across faces parallel to the rotary axis, in that each of the concave spaces is defined by a first face constituting a surface of the bottom wall portion, a second face comprised of a curved surface continuously erecting from a centrifugal side relative to the rotary axis of the first face, and a third face and a fourth face constituting an inner surface on the bottom wall portion side of the wall portions disposed at both sides of the bottom wall portion, and in that in the third and fourth faces, the third face provided at upstream of its rotational direction of the rotor is formed with a fifth face slanted toward the bottom wall portion by being cut out the opening side of the concave space.

According to the above-mentioned inventions, an area where the second air channel is provided may be larger than an area where the air supply port is provided in its circumferential direction around the rotary axis. In this case, the second air channel is provided is desirably formed in entire peripheral area except an area close to the exhaust port in its circumferential direction around the rotary axis.

In addition, the area where the second air channel is provided may be divided into a plurality of areas, and each first face of the areas may be disposed at different angle against its radiation direction of the rotary axis. In this case, it is desirable that a tangential angle of the first face as included in the each area is smaller toward downstream of its rotational direction of the rotor, relative to a tangential angle defined between a line extending from an end of the rotary axis side of the first face to the rotary axis side in the first face and a line extending from the end of the rotary axis side of the first face via the end of the rotary axis side to the rotation direction of the rotor.

In the above-mentioned inventions, the rotor may have a ring-like hub including a large-diameter ring portion and a small-diameter ring portion concentric therewith, and the first turbine blade portion may be provided at an outer circumference of the large-diameter ring portion, while the second turbine blade portion may be provided at an outer circumference of the small-diameter ring portion.

Advantageous Effects

According to the air-driven rotary cutting device of the present invention, an operator can hold the grip part and execute cutting operation with the head part at the tip end of the grip part directed to an objective region to be cut. The rotor is rotatably supported around the rotary axis via the bearing in the hollow portion formed in the head part, the rotor comprises a double-wheel rotor, the air emitted from the air supply port acts on the first turbine blade portion and the second turbine blade portion constituting the double-wheel rotor, and the energy is effectively utilized for rotation of the rotor. The air emitted from the air supply port into the first turbine blade portion acts on the first turbine blade portion to rotate the rotor around the axial center of the rotary axis and is guided to the second turbine blade portion by a guide part formed in the hollow portion in the head part. The air reached at the second turbine blade portion acts on the second turbine blade portion to further promote rotation of the rotor and then is discharged from the exhaust port. The air guided in the first turbine blade portion and the second turbine blade portion acts on the first turbine vane and the second turbine vane which are substantially formed therewith, respectively. In this case, the side shape of the first turbine vane seen in a direction facing into the rotary axis is concave from upstream to downstream in a rotational direction of the rotor, so that the energy of the air emitted from the air supply port is effectively used as power for rotating the rotor around the axial center of the rotary axis via the first turbine vane. The air reached the second turbine blade portion from the guide part acts on the second turbine vane to further promote rotation of the rotor. The side shape of the second turbine vane is concave in a direction opposite to that of the first turbine vane so that the air substantially acts along a convex curved surface of the second turbine vane. Therefore, the rotation promoting power by the introduced air in the second turbine blade portion is not so large and the increased degree of the rotational speed of the rotor is slight and the rotational speed of the rotor can be limited. However, the energy of the air emitted from the air supply port is effectively used in the first turbine blade portion, so that the rotary torque of the rotor can be adequately obtained.

When the second air channel is provided at the inner circumference of the hollow portion in the head part and is formed with a plurality of concave spaces defined with a plurality of wall portions parallel to the rotary axis and the bottom wall portion intersecting the face which is formed between the wall portions and is parallel to the rotary axis, a member constituting the air guide ring as shown in the Patent Citation 2 is not required and the head part can be downsized. In addition, when the concave space is formed with the first to fourth faces, it can be easily and accurately processed in a desired form only by cutting the inner circumference of the hollow portion in the head part. When the bottom wall portion is formed directing to a radiation direction from the axial center of the rotary axis, the process is more facilitated. In addition, when the bottom wall portion is obliquely directed so as to be distal into the downstream side in the rotational direction of the rotor with respect to the radiation direction from the axial center of the rotary axis, air can smoothly flow from the first air channel to the second air channel of the first turbine blade portion, thereby reducing the damage by pressure. Still further, when the connecting parts of the first and second faces and the third and fourth faces are continuously formed with the curved face, air can smoothly communicate in the second air channel without causing damage by pressure. In addition, the third face positioned at the upstream side in the rotational direction of the rotor is cut out on the opening side of the concave space, the fifth face inclined to the bottom wall portion is provided, and air can more smoothly communicate from the first air channel to the second air channel, thereby synthesizing the smoothness and the characteristic by the shape of the second turbine vane to remarkably control the rotational speed while keeping the rotary torque of the rotor.

Further according to the air-driven rotary cutting tool of the present invention, in addition to the effect unique to the double-wheel rotor such that the energy of the supplied air is effectively used for rotation of the rotor, the head part can be downsized and the rotor which has decreased rotational speed and keeps a required rotary torque can be obtained by the characteristic structure of the second air channel having the fifth face. According to the above-mentioned inventions, the second air channel is provided on the inner circumference of the hollow portion in the head part and is formed with a plurality of concave spaces formed by a plurality of wall portions parallel to the rotary axis and a bottom wall portion intersecting a face which is formed between the wall portions and is parallel to the rotary axis, and the air introduced in the first turbine blade portion is introduced in the concave space so as to be compressed accompanied with rotation of the rotor and at the same time guided to the second turbine blade portion, thereby always keeping positive pressure condition in the head part. Therefore, the suck back preventing function can be obtained when air supply is stopped and the rotation of the rotor is stopped as disclosed in the Patent Citations 3 and 4.

According to the above-mentioned inventions, when the area formed with the second air channel is larger than the area formed with the air supply port with respect to the circumferential direction around the rotary axis, the air emitted from the air supply port can surely flow into the second air channel via the first air channel. In this case, the area formed with the second air channel extends all the circumference except for the area close to the exhaust port with respect to the circumferential direction around the rotary axis, the air flown in the second air channel does not directly go to the exhaust port and it temporally stays in the second air channel, so that the above-mentioned suck back preventing effect can be more improved, and in addition, the air guided from the first turbine blade portion can be smoothly introduced into the second turbine blade portion from the second air channel, thereby controlling the rotational speed of the rotor while keeping the rotary torque.

Further according to the above-mentioned inventions, when the area formed with the second air channel comprises a plurality of areas, and each first face included in each area has a different angle with respect to the radiation direction of the rotary axis, the effect of the air flown in the second air channel in each area is different. Therefore, when the angle at each area is arbitrarily set, the air guide function into the third air channel and the temporarily air retention function in the second air channel are mixed to effectively execute reduction of the rotational speed of the rotor and prevention of suck back. Specifically when the tangential angle of the first face included in the each area is designed to be smaller into the downstream of the rotation direction of the rotor, wherein the tangential angle is defined between an extended line from the first face from the end on the rotary axis side of the first face into the rotary axis side and an extended line from the end on the rotary axis side of the first face through the end on the rotary axis side into the rotation direction of the rotor, the air can temporarily stay in the upstream side into the rotational direction of the rotor in the second air channel and can rapidly flow in the third air channel at the downstream side.

Further, when the rotor has a ring-like hub including a large-diameter ring portion and a small-diameter ring portion concentric with the large-diameter ring portion, and the first turbine blade portion is formed on an outer circumference of the large-diameter ring portion and the second turbine blade portion is formed on an outer circumference of the small-diameter ring portion, the double-wheel rotor can be easily processed.

BEST MODE FOR CARRYING OUT THE INVENTION

Figure 1:
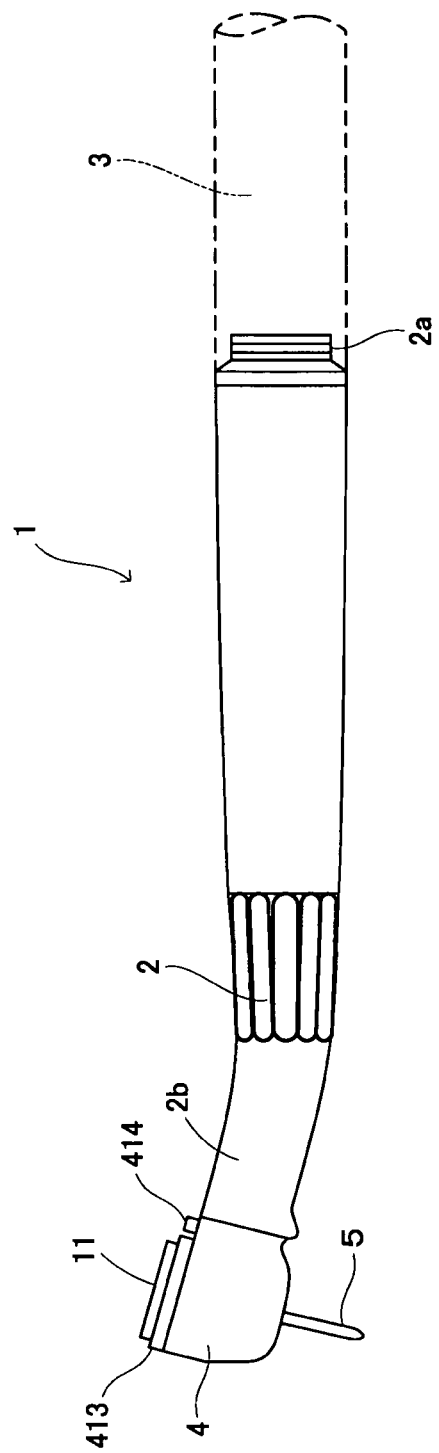
FIG. 1 is a side view of a dental air turbine handpiece as one embodiment of the air-driven rotary cutting tool of the present invention.
Figure 2:
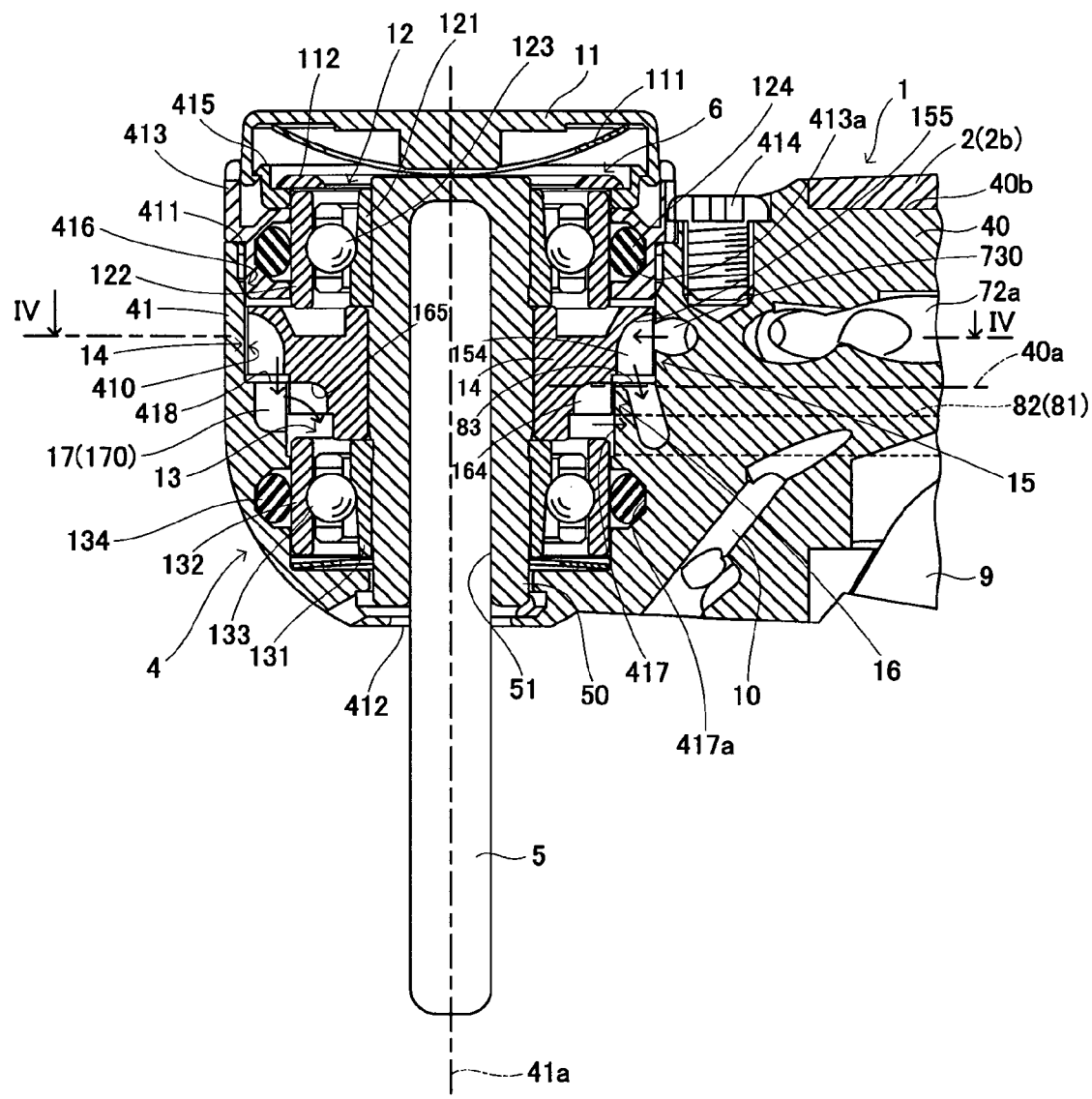
FIG. 2 is a vertical sectional view of the essential part of the dental air turbine handpiece.
Figure 3:
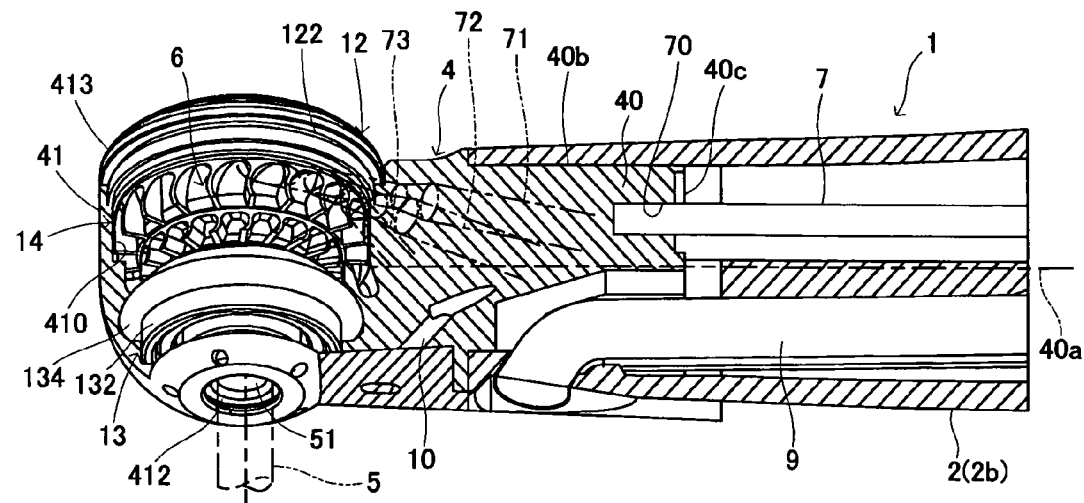
FIG. 3 is a partially broken, partially vertical, and partially perspective view of the essential part of the dental air turbine handpiece.
Figure 4:
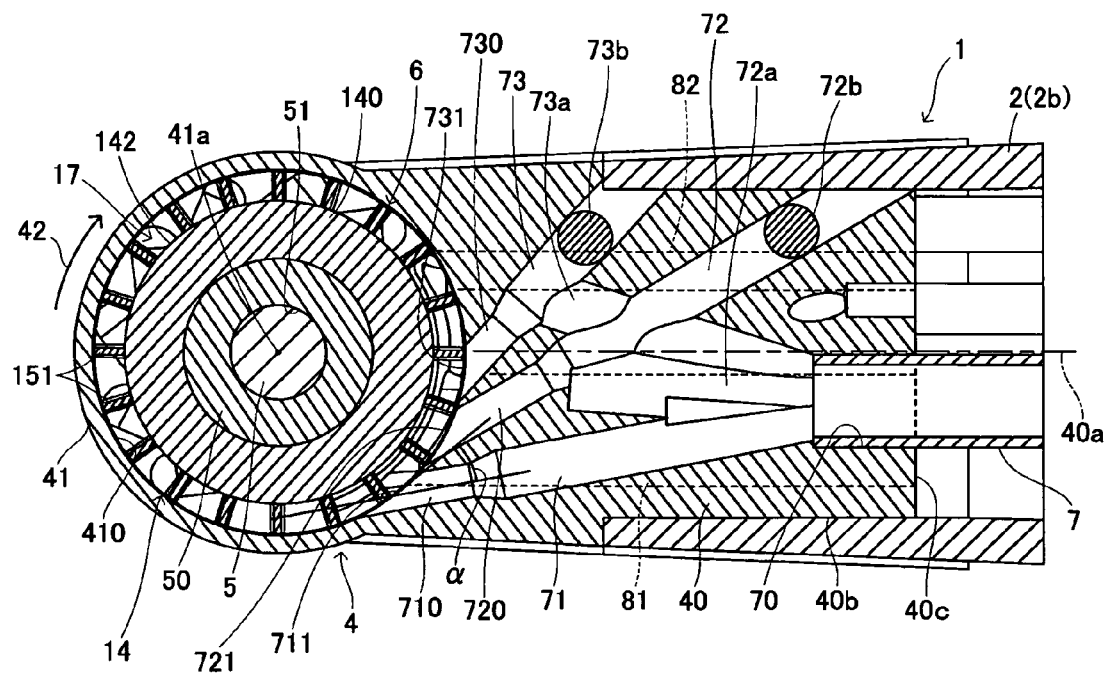
FIG. 4 is a fragmental sectional view along the line IV-IV in FIG. 2.

An embodiment of the air-driven rotary cutting tool of the present invention is explained referring to the attached drawings. FIG. 1 is a side view showing the entire structure of a dental air turbine handpiece as one embodiment of the air-driven rotary cutting tool of the present invention. In FIG. 1 the handpiece 1 has a grip part 2 held with a hand of an operator for medical treatment, the base end part of the grip part 2 is provided with a connecting part 2a for connecting with a supply tube 3 of acting medium such as air and water like a conventional handpiece, the tip end part of the grip part 2 is connected with a head part 4 via a neck part 2b. A cutting tool 5 is detachable to the head part 4. FIG. 2 to FIG. 4 are enlarged views of the head part 4 and therearound in FIG. 1. As shown in these figures, the head part 4 integrally has a shaft like body 40 connected to the tip end of the grip part 2, and a tubular housing 41 containing the cutting tool 5 and a driving part 6 for driving the cutting tool 5, and the center axis (corresponds to the rotary center of the cutting tool to be mentioned later, and refers to the rotary axis hereinafter) 41a of the tubular housing 41 is directed perpendicular or substantially perpendicular to the axial center 40a of the shaft like body 40.

The shaft like body 40 of the head part 4 has a small caliber part 40b processed so as to be shaped and sized to be inserted and fixed in the tip end of the tubular grip part 2 as shown in FIG. 2 to FIG. 4. The shaft like body 40 is provided with a plurality of penetrating apertures for fluidically communicating a rear end surface 40c (the end surface at right on the sheet of FIG. 3 and FIG. 4) on the grip part 2 side and the inner wall surface of the tubular housing part 41. The plurality of penetrating apertures include air supply passages 71-73 for supplying a pressurized air to the cutting tool driving part 6 and exhaust passages 81, 82 for discharging the pressurized air from the cutting tool driving part 6.

The air supply passages 71-73 are connected to an air supply pipe 7 from the connecting part 2a with the operating medium supply tube 3 shown FIG. 1 provided along the longitudinal axial direction of the grip part 2 in the grip part 2. Each air supply passage 71-73 is formed such that the shaft like body 40 is processed to have a hole in a predetermined length from the rear end surface 40c on the grip part 2 side and the outer circumferential surface of the small caliber part 40b into the inner wall surface of the tubular housing 41 as shown in FIG. 4. The air supply passage 71 communicates a connecting part 70 of an air supply pipe 7 drilled in the shaft like body 40 and the air supply passages 72, 73 communicate the connecting part 70 via connecting passages 72a, 73a drilled in the shaft like body 40. Accordingly, the pressurized air supplied from the air supply pipe 7 is introduced in the tubular housing part 41 via each air supply passage 71 to 73. The base ends of the air supply passages 72, 73 open to the outer circumferential surface of the small caliber part 40b, so that spherical sealing members (for example steel ball) 72b, 73b are pressed in the midstream on the open side of the air supply passages 72, 73 to seal thereof, respectively. The connecting passage 73a is formed so as to go across the air supply passage 72 to be communicated with the air supply passage 72 and also with the air supply passage 73 as shown in the figure. Each air supply passage 71 to 73 has a nozzle part 710, 720, 730 with small diameter at the tip end thereof and the tip end of each nozzle part 710, 720, 730 opens to the inner wall surface of the tubular housing part 41 to form an air supply port 711, 721, 731, respectively (also see FIG. 10). The nozzle parts 710, 720, 730 are preferably arranged in such a manner that the cutting tool 5 provided inside of the tubular housing part 41 receives rotating force in the direction shown with an arrow 42 around the rotary axis 41a (clock-wise direction in FIG. 4) by the pressurized air ejected from the nozzle parts 710, 720, 730. Specifically, the air supply ports 711, 721, 731 are aligned along the circumferential direction in the cylindrical inner surface of the tubular housing part 41 and the crossing angle (nozzle tangential angle: α) of the central axes of the nozzle parts 710, 720, 730 and the tangential line passing the point which is on the cylindrical inner surface of the tubular housing 41 and crosses the center axis is preferably set at about 10 to 50 degrees.

Each nozzle part 710, 720, 730 is connected to each air supply passage 71 to 73 via a tapered part, respectively, wherein the total transverse area of the connecting parts of the air supply passages 71 to 73 via the tapered parts becomes larger than the total transverse area of the opening of each nozzle part 710, 720, 730 into the inner wall surface of the tubular housing part 41. The angle of each tapered part (taper angle) is preferably about 15 to 45 degrees. In addition, the effective sectional area added with the transverse area of the nozzle parts 710, 720, 730 is preferably smaller than the effective sectional area of the air supply pipe 7.

Figure 10:
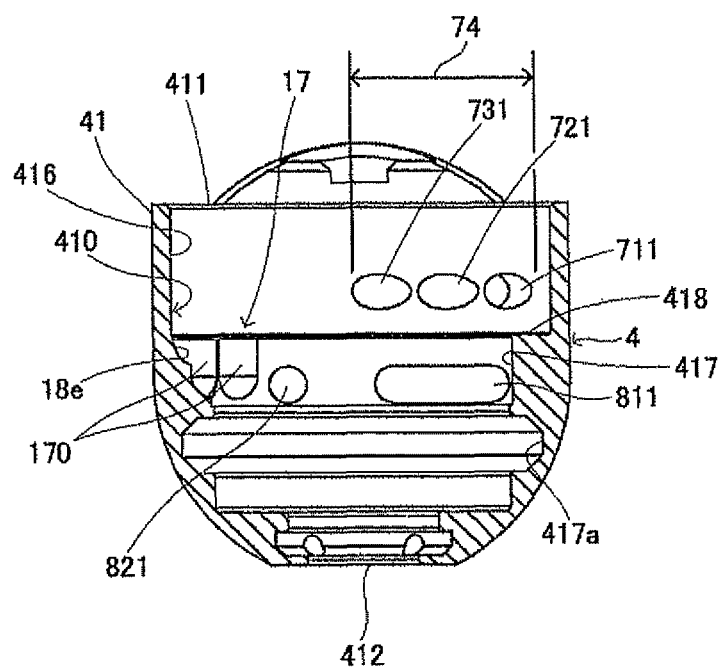
FIG. 10 is a fragmental sectional view along the line X-X in FIG. 6.

The air supply ports 711, 721, 731 are generally formed oval as shown in FIG. 10, however, the shape is not limited and may be rectangular (not shown). As mentioned above, the connecting part 70 is formed in parallel to the axial center 40a of the shaft like body 40 and the air supply pipe 7 for supplying a pressurized air is connected to the connecting part 70 via the connecting member. For this purpose, comparing to the case that the connecting part 70 is obliquely formed with respect to the axial center 40a of the shaft like body 40, the space adjacent to the rear end surface 40c at shaft part can be effectively utilized. The exhaust passages 81, 82 are formed under the air supply passages 71-73 as shown in FIG. 2 and comprise an aperture penetrating from the rear end surface 40c on the shaft into the inner wall surface of the tubular housing 41. The tip end parts of the exhaust passages 81, 82 open to the inner wall surface of the tubular housing part 41 to form exhaust ports 811, 821 (see FIG. 10) and the base end part opens to the rear end surface 40c at the shaft part and communicates with an exhaust means, not shown, via the connecting part 2a and the supply tube 3 using the inner tubular part of the grip part 2 as an exhaust passage shown in FIG. 1. Further, the shaft like body is provided with a light guide body 9 for illuminating the tip end part of the cutting tool 5 and a chip air pipe 10 for supplying water to the tip of the cutting tool 5. A water supply pipe and an air supply pipe to the chip air pipe 10 are not shown.

As shown in FIG. 2 and FIG. 3, the tubular housing part 41 of the head part 4 has a cylindrical hollow portion 410 shaped and sized corresponding to the external shape of the driving part 6 for converting the pressurized air emitted from the air supply passages 71-73 to the rotating force of the cutting tool 5. The inner hollow portion 410 is opened by upper and lower openings 411, 412 (also see FIG. 10). The driving part 6 is inserted in the hollow portion 410 from the upper opening 411, and the cutting tool 5 is detachable via the lower opening 412 to a tool supporting part 50, mentioned later, provided for the driving part 6 inserted in the hollow portion 410. The upper opening 411 is detachably provided with a ring-like sub-housing 413 so as to keep the driving part 6 at a predetermined position in the hollow portion 410. A male screw is provided at the outer circumferential part of the sub-housing 413 and is screwed to a female screw formed at the inner circumferential part of the opening 411, and the screwed condition is locked with a screw 414 attached to the head part 4 (also see FIG. 1). Further, a cap supporting ring 415 is provided on the upper surface of the sub-housing 413 and a cap 11 is detachably provided on the opening 411 by the cap supporting ring 415. The cap supporting ring 415 allows the up-and-down movement of the cap 11 along the rotary axis 41a, on the other hand, it engages the circumferential part of the cap 11 so as to prevent the cap 11 from falling out upward. In this embodiment, as shown in FIG. 2, a spring member (wave washer in the figure) 111 is elastically provided between the inside of the cap 11 and the driving part 6 and the cap 11 is stably kept in a position shown in the figure by the urging power of the spring member 111. The spring member 111 in an elastically provided condition acts on a press ring 112 provided so as to be astride an outside ring 122 of an upper bearing 12, mentioned later, and the cap supporting ring 415 and makes the driving part 6 kept at a predetermined position. When the cap 11 is pressed against the elasticity of the spring member 111, the cutting tool 5 can be exchanged while releasing the cutting tool 5 from the tool supporting part (for example, a chuck) 50.

The driving part 6 of the cutting tool 5 has the tool supporting part 50 supporting the cutting tool 5 along the rotary axis 41a of the inner hollow portion 410 as shown in FIG. 2. The tool supporting part 50 is formed with a hole (tool supporting hole) 51 having a predetermined depth from one end (the lower end in FIG. 2 and FIG. 3). The tool supporting part 50 is provided with a chuck mechanism (not shown) for holding the cutting tool 5 inserted in the tool supporting hole 51. The chuck mechanism is well known such that the cutting tool 5 is released to be exchangeable when the cap 11 is pressed. The cutting tool 5 is locked when the cap 11 is not pressed and is unlocked when the cap 11 is pressed so as to exchange the cutting tool 5. The tool supporting part 50 is not limited to the chuck mechanism and may be designed to be exchangeably held by the friction action of an elastic member like a rubber.

The tool supporting part 50 is rotatably supported by the upper bearing portion 12 and a lower bearing portion 13 provided up and down thereof, respectively, around the rotary axis 41a. The upper bearing portion 12 and the lower bearing portion 13 basically have the same structure and apply a well known ball bearing in this embodiment. However, the structure of the bearing is not limited to a ball bearing and other bearing structure (for example, a plain bearing, an air bearing and the like) may be used. Specifically, the upper bearing portion (ball bearing) 12 has an inner ring 121, an outer ring 122 provided concentric with the inner ring 121, and a plurality of balls 123 provided between the inner ring 121 and the outer ring 122. The inner ring 121 is externally fixed to the tool supporting part 50. On the other hand, the outer ring 122 is fixed in a pressed condition to the sub-housing 413 via an O-ring 124. The inner circumferential part of the sub-housing 413 is formed with a circumferential groove 413a for containing the O-ring 124. The O-ring 124 prevents the pressurized air emitted to the rotor 14, mentioned later, from leaking upward.

The lower bearing portion 13 is a ball bearing like the upper bearing portion 12 and has an inner ring 131, an outer ring 132 and a plurality of balls provided therebetween like the upper bearing 12. The inner ring 131 is externally fixed to the tool supporting part 50. On the other hand, the outer ring 132 is fixed in a pressed condition to the inner hollow portion 410 of the tubular housing 41 via an O-ring 134. The O-ring 134 prevents the pressurized air from leaking downward. The inner hollow portion 410 of the tubular housing 41 is shaped and sized corresponding to the area where the upper bearing portion 12, the lower bearing portion 13 and the rotor 14, mentioned later, are provided and comprises an upper tubular part 416 with large inner diameter, a lower tubular part 417 with small inner diameter, and a step part 418 formed between both tubular parts 416, 417. The O-ring 134 provided for the lower bearing portion 13 is contained in a circumferential groove 417a formed on the inner circumference of the lower tubular part 417.

Figure 5:
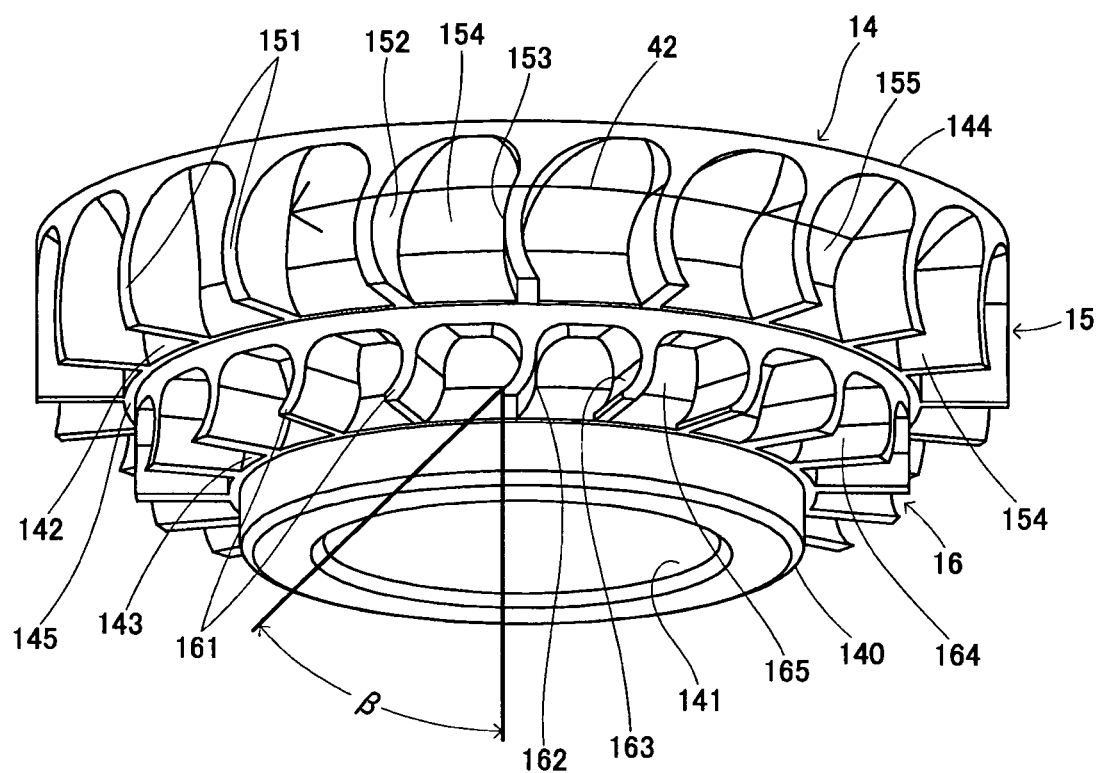
FIG. 5 is a perspective view showing one embodiment of a rotor incorporated to the dental air turbine handpiece.

The rotor 14 is explained also referring to FIG. 5. A double-wheel rotor 14 is integrally provided in the area between the upper bearing portion 12 and the lower bearing portion 13 of the tool supporting part 50 and the rotor 14 rotates the tool supporting part 50 and the cutting tool 5 around the rotary axis 41a via the tool supporting part 50 utilizing the pressurized air ejected from the air supply passages 71-73. The rotor 14 comprises a ring-like hub 140 as shown in the perspective view of the rotor part in FIG. 5 and the ring-like hub 140 is provided with a penetrating hole 141 at the center, an upper large-diameter ring portion 142 and a lower small-diameter ring portion 143 in concentric manner. The inner diameter of the penetrating hole 141 is almost same as the outer diameter around the middle part of the tool supporting part 50 supporting the rotor 14, when the middle part of the tool supporting part 50 is pressed into the penetrating hole 141, the rotor 14 and the tool supporting part 50 are integrated. Such integration includes shrinkage fit, caulking, key binding and the like. The large-diameter ring portion 142 and the small-diameter ring portion 143 are integrated up and down, the outer circumferential part of the upper large-diameter ring portion 142 is provided with the first turbine blade portion 15, and the outer circumferential part of the lower small-diameter ring portion 143 is provided with the second turbine blade portion 16.

The first turbine blade portion 15 comprises a circular upper ceiling wall 144 formed at the upper end of the hub 140 and a plurality of (18 in this embodiment) projected walls (the first turbine vane 151) which extend downward along the outer circumferential part of the large-diameter ring portion 142 from the bottom (lower surface) of the upper ceiling wall 144 and project outside in the radial direction. The first turbine vane 151 is provided at regular intervals along the circumferential direction of the large-diameter ring portion 142. Each first turbine vane 151 has one surface (a working surface 152 positioned at the upstream side of the rotor 14 along the rotational direction 42) of the turbine vane 151 and the other surface (a guide surface 153 positioned at the downstream side of the rotor 14 along the rotational direction 42) and a first air channel 154 is formed between each adjacent first turbine vane 151 with the working surface 152, the guide surface 153, the lower surface of the upper ceiling wall 144, and the outer circumferential part of the large-diameter ring portion 142. The height position of the first air channel 154 (height position along the rotary axis 41a) is set where the pressurized air emitted from the air supply nozzle parts 710, 720, 730 blows into the upper part of the first air channel 154 while the rotor 14 is provided in the inner hollow portion 410. The area from the lower surface of the upper ceiling wall to the outer circumferential part of the large-diameter ring 142 of the first air channel 154 is formed as a curved surface 155 curved into the inside of the radial direction (curved shape is well shown in FIG. 2), so that the air blown into the first air channel 154 from the outside of the radial direction of the rotor 14 is smoothly directed downward along the curved surface 155 with a minimum air resistance. The side shape of each first turbine vane 151 seen in a direction into the rotary axis 41a is concave into the downstream side from the upstream side of the rotational direction 42 of the rotor 14.

The second turbine blade portion 16 comprises a lower ceiling wall 145 whose outer circumference is bordered with the lower and inner edge of the first air channel 154 and a plurality of (18 in this embodiment) projected walls (the second turbine vane 161) which extend downward along the outer circumferential part of the small-diameter ring portion 143 from the bottom of the lower ceiling wall 145 and project outside into the radial direction. The second turbine vane 161 is provided at regular intervals along the circumferential direction. Each second turbine vane 161 has one surface (a working surface 162 positioned at the upstream side of the rotor 14 along the rotational direction 42) of the second turbine vane 161 and the other surface (a guide surface 163 positioned at the downstream side of the rotor 14 along the rotational direction 42) and the third air channel 164 is provided between each adjacent second turbine vane 161 with the working surface 162, the guide surface 163, the lower surface of the lower ceiling wall 145, and the outer circumferential part of the small-diameter ring portion 143. Specifically, the area from the lower surface of the lower ceiling wall 145 to the outer circumferential part of the small-diameter ring 143 of the third air channel 164 is formed as a curved surface 165 curved into the inside of the radial direction (curved shape is well shown in FIG. 2), so that the air blown into the third air channel 164 from the outside of the radial direction of the rotor 14 is smoothly directed downward along the curved surface 165 with a minimum air resistance. The height position of the third air channel 164 (height position along the rotary axis 41a) is set where the bottom of the third air channel 164 comes level with the exhaust passages 81, 82 when the rotor 14 is provided in the inner hollow portion 410. The side shape of each second turbine vane 161 seen in a direction into the rotary axis 41a is concave opposite to that of the first turbine vane 151. The lower piece of the second turbine vane 161 is bent so as to direct the rotational direction 42 and the bent angle β relative to the direction parallel to the rotary axis 41a is set larger than zero degree and smaller than 70 degrees.

As shown in FIG. 2, an air guide part 17 for guiding the air from the first turbine blade portion 15 into the second turbine blade portion 16 is provided on the inner circumference of the inner hollow portion 410 of the head part 4, specifically at the step part 418. The guide part 17 is explained also referring to FIG. 6 to FIG. 10. The pressurized air emitted into the inner hollow portion 410 from the air supply passages 71-73 is guided from the outside to the inside of the radial direction into the first air channel 154 and the pressurized air discharged from the lower end of the first air channel 154 is guided from the outside to the inside of the radial direction into the third air channel 164. The guide part 17 comprises a plurality (17 in the figure) of second air channels 170 for guiding air from the lower end of the first air channel 154 to the third air channel 164, the plurality of air passages 170 are arranged in the circumferential direction around the rotary axis 41a, and the formed area 171 extends all around the circumferential direction except for the area close to the exhaust ports 811, 821 along the circumferential direction (see FIG. 6). In addition, the area 171 formed with the second air channels 170 does not include the area 74 formed with the air supply ports 711, 721, 731 of the air supply passages 71-73 and is larger than the area 74 where the air supply ports 711, 721, 731 are provided (see FIG. 4 and FIG. 6).

The plurality of air passages 170 are formed from the step part 418 of the inner hollow portion 410 to the inner circumference of the small-diameter tubular part 417. When the driving part 6 is contained in the hollow portion 410, the first turbine blade portion of the rotor 14 is designed to be fitted in the inner circumferential part of the large-diameter tubular part 416 with a slight gap and the second turbine blade portion 16 is designed to be fitted in the inner circumferential part of the small-diameter tubular part 417 with a slight gap. The air supply ports 711, 721, 731 are opened to the inside of the large-diameter tubular part 416 and positioned so as to face the first air channel 154, and the exhaust ports 811, 821 are opened to the inside of the small-diameter tubular part 417 and are positioned at the lower end part of the third air channel 164. Further, an auxiliary exhaust port 83 communicated with the exhaust ports 81, 82 is opened like a long-hole at the region corresponding to the exhaust passages 81, 82 of the step part 418 and a part of air guided in the first air channel 154 is designed not to direct into the second and third air channels 170, 164 and to be directly discharged from the exhaust passages 81, 82.

Figure 8:
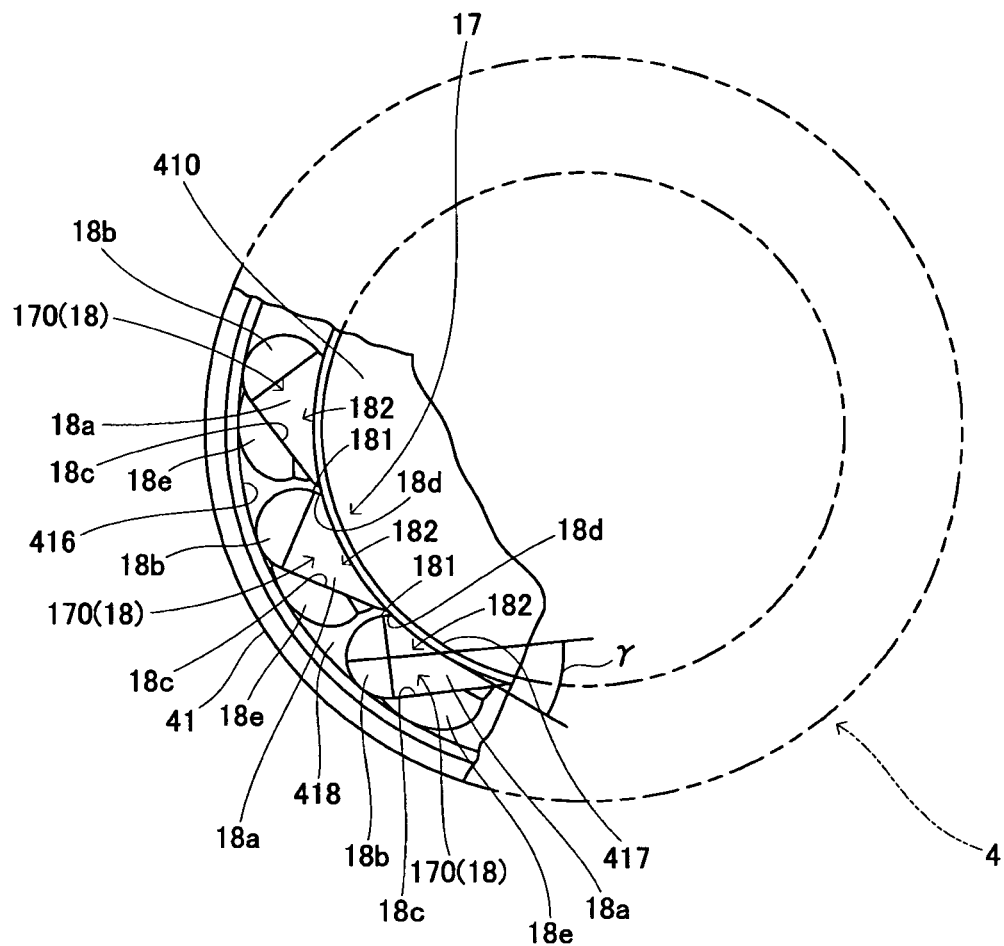
FIG. 8 is an enlarged view of the area enclosed with line VIII in FIG. 6.
Figure 9:
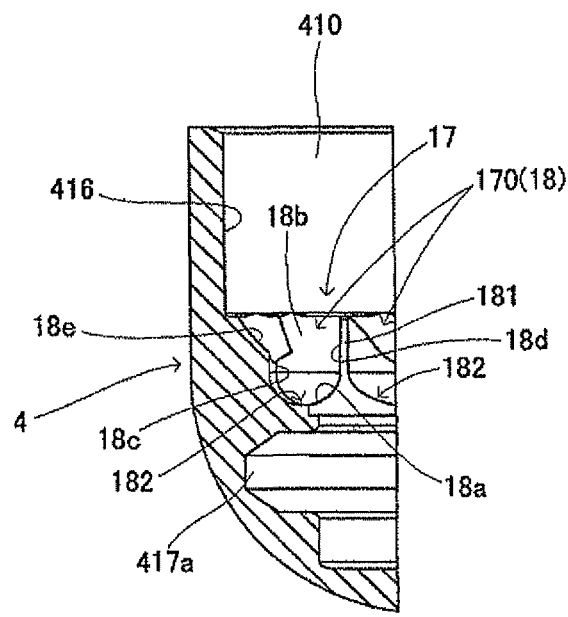
FIG. 9 is an enlarged view of the area enclosed with line IX in FIG. 7.

The second air channel 170 is provided at the inner circumference of the inner hollow portion 410 formed in the head part 4 and comprises a plurality of concaved spaces 18 formed with a plurality of wall portions 181 parallel to the rotary axis 41a and a bottom wall portion 182 which is formed between the wall portions 181 and passes over the surface parallel to the rotary axis 41a. The concaved space 18 is formed with the first face 18a constituting the surface of the bottom wall portion 182, the second face 18b constituted with a curved face continuously connected from the centrifugal side part of the first face 18a relative to the rotary axis 41a, and the third and the fourth faces 18c, 18d constituting the inside on the bottom wall side of the wall portion 181 positioned at both sides of the bottom wall portion 182. On the third face 18c positioned at the upstream side of the rotor 14 in the rotational direction 42 among the third and the forth faces 18c, 18d, an upward opening part of the concaved space 18 is cut out and the fifth face 18e inclined into the bottom wall portion 182 is formed. When the fifth face 18e is thus formed, the fluidity of air from the first air channel 154 to the second air channel 170 is improved, thereby effectively controlling the rotational speed of the rotor 14 and preventing such back. In addition, the bottom wall portion 182, namely the first face 18a, is directed from the axial center of the rotary axis 41a into the radial direction and is also obliquely directed so as to be centrifugal into the downstream side of the rotational direction 42 of the rotor 14, along the radial direction. When the first face 18a is thus obliquely formed so as to be centrifugal into the downstream side of the rotational direction 42 of the rotor 14, the flown air is apt to temporarily stay in the concaved space 18, thereby further improving the above-mentioned suck back prevention. As shown in FIG. 8, the angle (tangential angle) γ formed with the center line of the first face 18a and the tangential line where the center line crosses the inner circumference of the small-diameter tubular part 417 is set from 45 degrees to 60 degrees. The connecting parts of the first and second faces 18a, 18b and the third and forth faces 18c, 18d are continuously formed with a curved face and air can smoothly communicate in the second air channel 170 without causing damages by pressure. The curvature radius of the curved face of the connecting part is preferably equal to or larger than 0.1 mm.

When teeth are cut with thus constructed handpiece 1, a cutting tool 5 suitable for an objective operation is selected as shown in FIG. 1 and is fitted to the tool supporting part 50 from downward. Next, a pressurized air supplied from a pressurized air supply source, not shown, is supplied to each air supply passage 71-73 via the supply tube 3. Then, the pressurized air is supplied from each air supply passage 71-73 to the nozzle parts 710, 720, 730. The pressurized air passing through the nozzle parts 710, 720, 730 is accelerated, directed in perpendicular to the rotary axis 41a of the rotor 14 (downstream side of the rotational direction 42 of the rotor 14), and is emitted from the air supply ports 711, 721, 731. When the pressurized air is blown into the first air channel 154, the energy of the pressurized air is applied on the working surface 152 of the first turbine vane 151 of the first turbine blade portion 15 as shown in FIG. 5, and the rotor 14 is rotated in the direction of the arrow 42 around the axial center of the rotary axis 41a of the rotor 14. Accompanied with this rotation, the pressurized air is sequentially blown into the first air channel 154 running opposite to the air supply ports 711, 721, 731 and the rotor 14 keeps rotating. The side shape of the first turbine vane 151 is in concave shape dent to the rotational direction 42, so that the energy of the pressurized air blown into the first air channel 154 acts on the working surface 152 and is effectively expended as the rotating force of the rotor 14. Therefore, in this stage, the rotor 14 rotates at high rotational speed while keeping a large rotary torque.

The pressurized air supplied in the first air channel 154 flows downward in the first air channel 154 between each first turbine vane 151. When it moves to a position where the first air channel 154 is formed at the tubular housing part 41 of the head part 4 and which is opposite to the second air channel 170, it flows into the second air channel 170 from the opening at the bottom of the first air channel 154. The fifth face 18e is provided at upstream side of the concaved recess 18 and is formed so as to incline into the first face 18a (bottom wall portion 182), so that air entry into the second air channel 170 can be executed smoothly. The air entered in the second air channel 170 is directed to the inside of the radius of the rotor 14 along the first to fifth faces 18a to 18e of the concaved space 18 forming the second air channel 170, and is supplied to the third air channel 164 of the rotor 14. The concaved space 18 is formed such that the first face 18a is inclined with an angle γ in the centrifugal direction as shown in FIG. 8, so that the air flowing in the concaved space 18 is apt to temporally stay therein and is supplied to the third air channel 164 while keeping high inner pressure. The pressurized air flown in the third air channel 164 is guided between each second turbine vane 161 forming the third air channel 164 and the inside curved surface 165 interposed therebetween to move downward, and is supplied to the exhaust passages 81, 82 via the exhaust ports 811, 821. The air supplied to the exhaust passages 81, 82 is discharged outside via the acting medium supply tube 3 connected to the handpiece 1.

The pressurized air in the third air channel 164 acts on the working surface 162 of the second turbine vane 161 constituting the second turbine blade portion 16, and further promotes rotation of the rotor 14. However, the side shape of the second turbine vane 161 is concave so as to be dent in the opposite direction of that of the first turbine vane 151, the working surface 162 of the second turbine vane 161 becomes a convex surface against the working air flow, and the air flown in the third air channel 164 acts so as to flow along the convex surface. Therefore, the rotation propulsion force by the air introduced in the second turbine blade portion 16 is not so large and the degree of improving the rotational speed of the rotor 14 is small, thereby reducing the rotational speed of the rotor 14. However, the rotor 14 has enough rotary torque by the action of the pressurized air on the first turbine blade portion 15, so that it keeps the cutting ability required for cutting teeth. In addition, the rotational speed of the rotor 14 is controlled to be under the durable rotational speed of the cutting tool 5, thereby eliminating the fear of bent damage and projecting out of the tool holding part 50 of the cutting tool 5. In addition, the noise and heat generated at cutting operation are reduced and a patient does not feel discomfort. When the pressurized air is stopped emitting, the rotation of rotor 14 is stopped, however, the concaved space 18 is always filled with air to keep high inner pressure during rotation of the rotor 14, so that suck back is not caused when emission of the pressurized air is stopped and cut chip and treatment liquid are not suck in the mechanism of the head part 7 from the cutting region of tooth.

Figure 11:
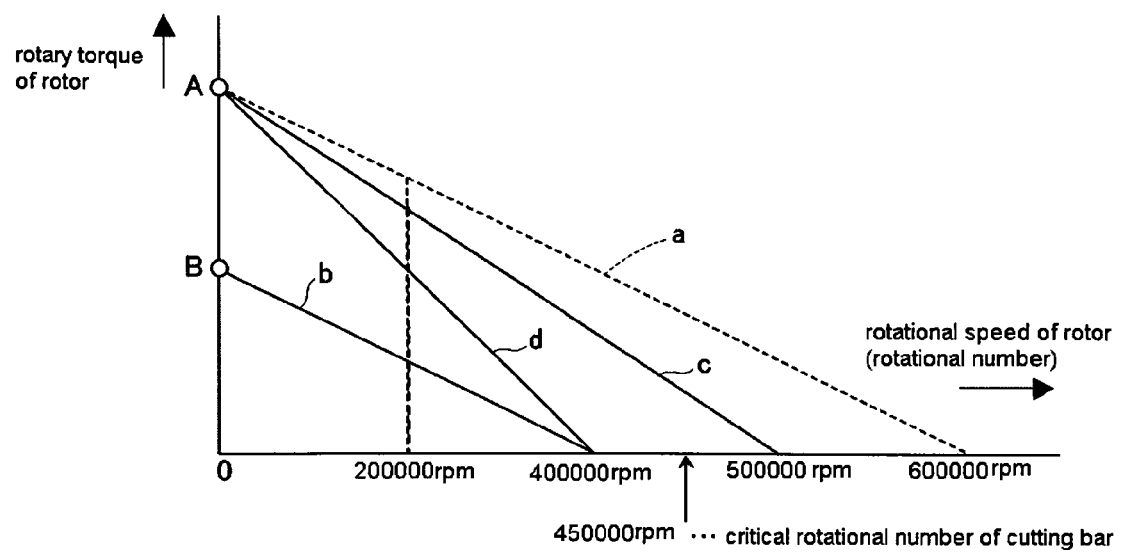
FIG. 11 is a graph showing the relation of the rotational speed and the rotary torque of the rotor of the dental air turbine handpiece together with a comparative example.

The functional characteristic of a dental air turbine handpiece wherein the rotary torque of the rotor is substantially kept and the rotational speed is lowered is explained referring to FIG. 11. FIG. 11 is a graph showing the relation of the rotational speed of the rotor and the torque applied on the tooth when the cutting tool is acted on the tooth while rotating the rotor. As understood from this graph, when the cutting tool is acted on the tooth from no-load condition and the acting force is enlarged, the rotational, speed of the rotor is reduced, however, the load on the tooth, namely torque, is enlarged. When the rotational speed becomes zero, the torque becomes maximum, which is called lock torque and is emphasized in the clinical practice. The increase of the lock torque strengthen the cutting force of tooth and it is generally the torque of the air turbine handpiece is high.

The graph "a" in FIG. 11 shows the sample of a conventional air turbine handpiece, when the lock torque is to be the level A in this case, the rotational speed (rotational number, hereinafter) of the rotor at no-load is required to be about 600,000 rpm. The rotational speed goes far beyond the critical rotational speed of 450,000 rpm and the above-mentioned fear may arise. When the pressure of the pressurized air emitted into the rotor is lowered to make the rotational speed at 400,000 rpm as shown in the graph "b", the lock torque is lowered to the level B and the cutting ability of tooth is deteriorated, thereby degrading the practical performance as an air turbine handpiece. The graph "c" shows that the rotational speed of the rotor is reduced without lowering the lock torque by devising the structure of the rotor as proposed in the Patent Citation 2 and the cutting ability of tooth is not deteriorated. However, the rotational speed of the rotor cannot lower the critical rotational speed of the cutting tool and the fear of defect of the cutting tool cannot be cleared. The graph "d" shows the relation of the air turbine handpiece 1 having the above-mentioned structures and the rotational speed of the rotor can be 400,000 rpm while keeping the lock torque at level A. Comparing the graphs "a" and "c" with the graph "d" in FIG. 11, when the rotational speed of the rotor is 200,000 rpm, the torque value of the graph "d" is lower than that of the graphs "a" and "c". However, the lock torque is same at level A, so that the actual cutting ability does not differ and an operator does not feel difference in cutting.

As mentioned above, the characteristic structures of the first turbine vane 151 and the second turbine vane 161 constituting the rotor 14 and the second air channel 170 are synthesized, and the rotational speed of the rotor 14 can be reduced while keeping the torque. Accordingly, the rotor 14 can have a small diameter, the head part 4 can be downsized, and the applicability of the dental air turbine handpiece 1 can be dramatically improved. In addition, because the second air channel 170 is directly formed in the inner hollow portion 410 of the head part 4, the space in the hollow portion 410 is effectively used, thereby more contributing downsizing.

Figure 6:
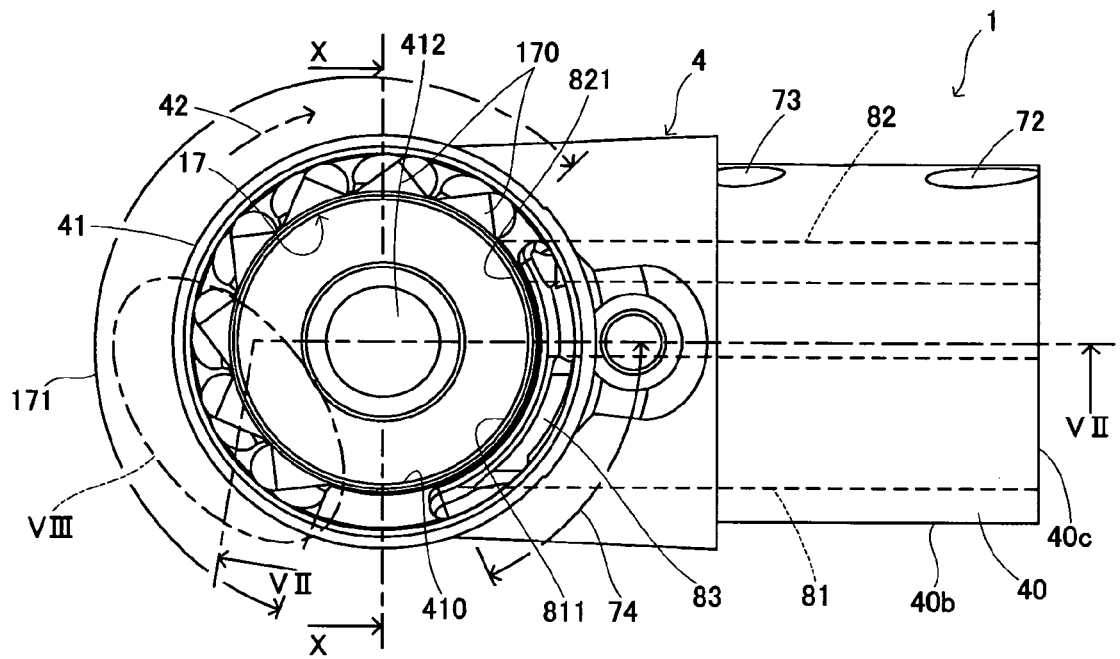
FIG. 6 is a plan view of a head part of the dental air turbine handpiece.
Figure 7:
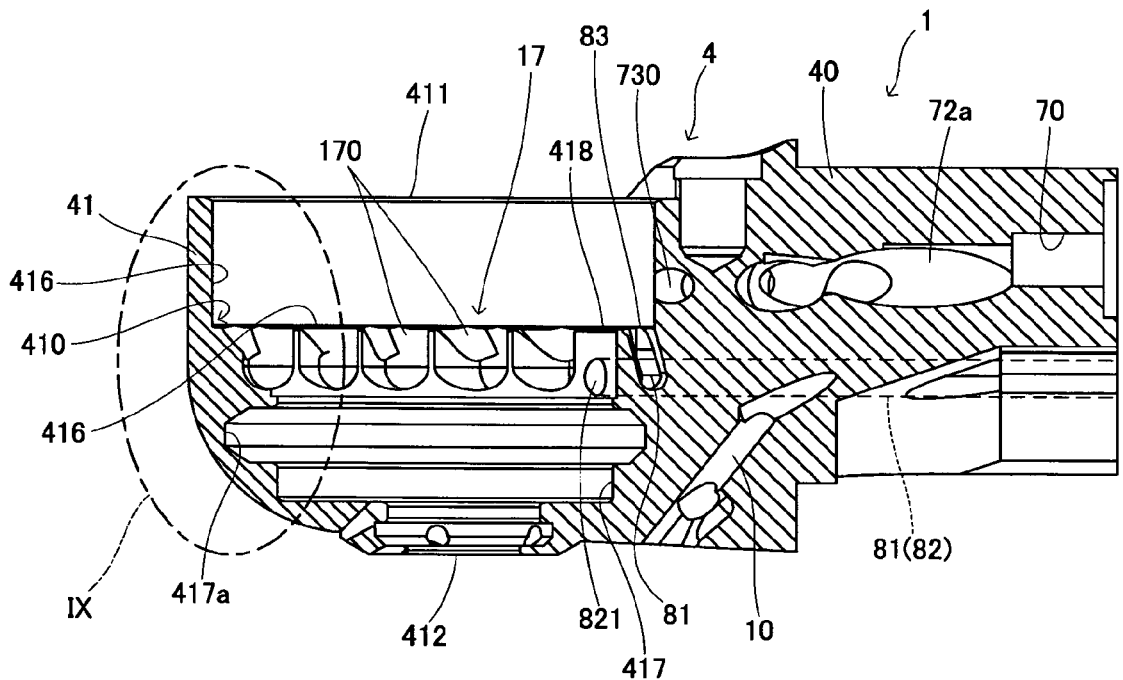
FIG. 7 is a fragmental sectional view along the line VII-VII in FIG. 6.
Figure 12:
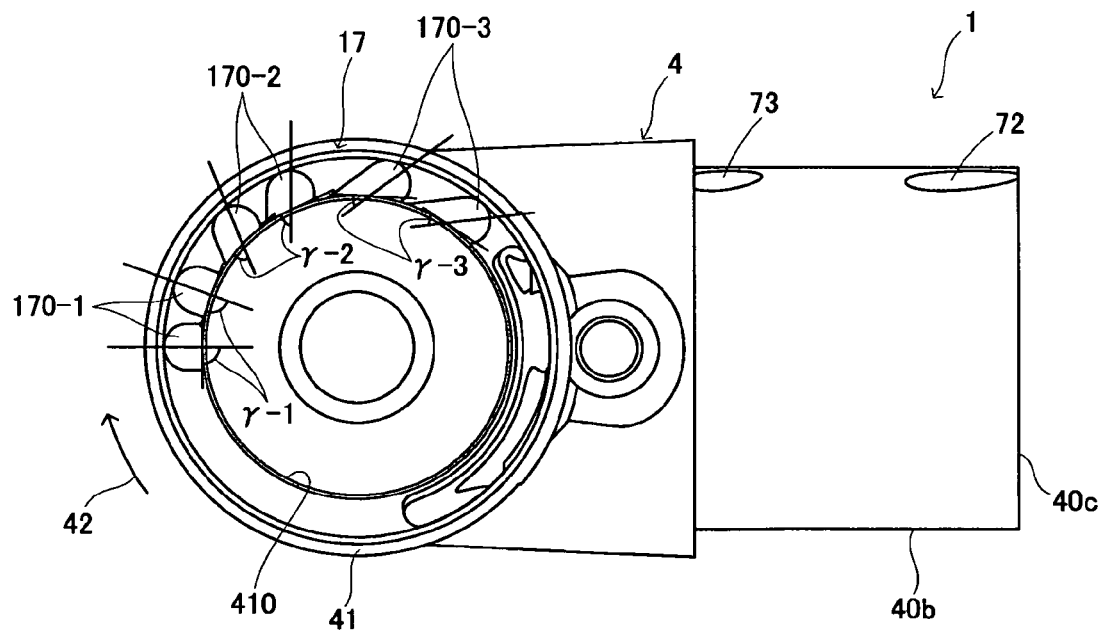
FIG. 12 is a diagrammatic plan view showing another embodiment of the head part.

FIG. 12 is a plan view showing another embodiment of the head part 4 and is shown as the diagrammatic view corresponding to FIG. 6. In this embodiment, the area where a plurality (6 in the figure) of second air channels 170 are formed comprises plural areas, and each first face included in each area has a different angle with respect to the radial direction of the rotary axis. Namely, the angle corresponds to the angle (tangential angle) γ in FIG. 8 and six second air channels 170 are arranged such that two of them form a pair (170-1, 170-2, 170-3) from the upstream to the downstream of the rotational direction 42, each pair constitutes the area, and the angle γ in each area becomes smaller into the downstream of the rotational direction 42 of the rotor 14 like γ-1, γ-2, γ-3. When the angle γ is designed to become smaller into the downstream side of the rotational direction 42 of the rotor 14, air temporally stays in the second air channel 170 at the upstream side of the rotational direction 42 of the rotor 14, and air can rapidly flow in the third air channel 164 at the downstream side. Therefore, control of the rotational speed of the rotor 14 and prevention effect of suck back can be appropriately balanced.

In FIG. 12 six second air channels 170 are split into pairs by which a plurality of areas are formed, and the tangential angle γ of each area is sequentially differed into the downstream side, however, the structure of the area is not limited to this. For example, each area may be constituted with one second air channel 170 or the number of the second air channels 170 contained in each area may be differed.

Each second passage 170-1, 170-2, 170-3 in FIG. 12 has the concaved space 18 having the first to fifth faces 18*a* to 18*e* as mentioned above, although the reference numerals are not shown. Other structures are same as FIG. 6 and the same reference numerals are allotted and their explanation is omitted.

The dental air turbine handpiece is exemplified in the above-mentioned embodiment, however, the present invention can be applied to other air-driven rotary cutting tool used by an operator. The number of the first and second turbine vanes 151, 161 constituting the first and second turbine blade portions 15, 16 and the number of the second air channel 170 constituting the air introduction part 17 are not limited in those shown in the drawings.

The invention claimed is:

1. An air-driven rotary cutting tool comprising:
a grip part adapted to be held by an operator;
a head part provided at a distal end of said grip part; and
a rotor provided in a hollow portion formed in said head part with a bearing in between said rotor and said head part, said rotor being rotatable around a rotary axis thereof:
said rotor comprising a first turbine blade portion provided with a plurality of first turbine vanes surrounding said rotary axis and a second turbine blade portion integrally formed with said first turbine blade portion and having a plurality of second turbine vanes surrounding said rotary axis;
said head part including in said hollow portion an air supply port for emitting air into said first turbine blade portion of said rotor from an air supply passage provided at said grip part, a guide portion for guiding air from said first turbine blade portion into said second turbine blade portion, and an exhaust port for exhausting air from said second turbine blade portion to an exhaust passage provided at said grip part; and
air emitted from said air supply port blowing into a first air channel provided between said first turbine vanes and activating said first turbine blade portion from a substantially perpendicular direction relative to said rotary axis of said rotor to rotate said rotor around an axial center of said rotary axis and being exhausted from said first air channel of said first turbine blade portion along an axial direction of said rotary axis, the air further being guided by a second air channel provided at said guide portion into a third air channel provided between said second turbine vanes of said second turbine blade portion, the air thus guided into said third air channel of said second turbine blade portion activating said second turbine blade portion in a direction substantially perpendicular to said rotary axis to further promote rotation of said rotor, and then the air being exhausted from said third air channel and into said exhaust port; wherein
each of said plurality of first turbine vanes has such a concave shape on a side thereof seen in a direction into said rotary axis as to be concaved from an upstream side into a downstream side in a rotational direction of said rotor, while each of said second turbine vanes has such a concave shape on a side thereof as to fall be concaved into an opposite direction from said first turbine vanes.

2. The air-driven rotary cutting tool as set forth in claim 1, wherein:
said second air channel comprises a plurality of concave spaces defined by:
a plurality of wall portions, which are formed on an inner circumference of said hollow portion of said head part and are parallel to said rotary axis, and
a bottom wall portion, which is formed between said plurality of wall portions and across planes parallel to said rotary axis; and
each of said plurality of concave spaces is defined by:
a first face constituting a surface of said bottom wall portion,
a second face comprised of a curved surface continuously erecting from a centrifugal side of said first face relative to said rotary axis, and
a third face and a fourth face constituting inner surfaces on a bottom wall portion side of said wall portions disposed at both sides of said bottom wall portion.

3. The air-driven rotary cutting tool as set forth in claim 2, wherein said bottom wall portion is directed from said axial center of said rotary axis in a radial direction.

4. The air-driven rotary cutting tool as set forth in claim 2, wherein said bottom wall portion is obliquely directed, with respect to a radial direction from said axial center of said rotary axis, so as to be centrifugal into said downstream side of said rotational direction of said rotor.

5. The air-driven rotary cutting tool as set forth in any one of claims 2 to 4, wherein connecting portions of said first and second faces and of said third and fourth faces are continuously formed with a curved surface.

6. The air-driven rotary cutting tool as set forth in claim 5, wherein said third face provided on an upstream side in said rotational direction of said rotor is formed with a fifth face slanted toward said bottom wall portion and formed by cutting out an opening side of said concave space.

7. An air-driven rotary cutting tool comprising:
a grip part adapted to be held by an operator;
a head part provided at a distal end of said grip part; and
a rotor provided in a hollow portion formed in said head part with a bearing in between said rotor and said head part, said rotor being rotatable around a rotary axis thereof:
said rotor comprising a first turbine blade portion provided with a plurality of first turbine vanes surrounding said rotary axis and a second turbine blade portion integrally formed with said first turbine blade portion and having a plurality of second turbine vanes surrounding said rotary axis;
said head part including in said hollow portion an air supply port for emitting air into said first turbine blade portion of said rotor from an air supply passage provided at said grip part, a guide portion for guiding air from said first turbine blade portion into said second turbine blade portion, and an exhaust port for exhausting air from said second turbine blade portion to an exhaust passage provided at said grip part; and
air emitted from said air supply port blowing into a first air channel provided between said first turbine vanes and activating said first turbine blade portion from a substantially perpendicular direction relative to said rotary axis of said rotor to rotate said rotor around an axial center of said rotary axis and being exhausted from said first air channel of said first turbine blade portion along an axial direction of said rotary axis, the air further being guided by a second air channel provided at said guide portion into a third air channel provided between said second turbine vanes of said second turbine blade portion, the air thus guided into said third air channel of said second turbine blade portion activating said second turbine blade portion in a direction substantially perpendicular to said rotary axis to further promote rotation of said rotor, and then the air being exhausted from said third air channel and into said exhaust port; wherein
said second air channel comprises a plurality of concave spaces defined by:
a plurality of wall portions, which are formed on an inner circumference of said hollow portion of said head part and are parallel to said rotary axis; and
a bottom wall portion, which is formed between said plurality of wall portions and across planes parallel to said rotary axis,
each of said plurality of concave spaces is defined by:
a first face constituting a surface of said bottom wall portion;
a second face comprised of a curved surface continuously erecting from a centrifugal side of said first face relative to said rotary axis; and
a third face and a fourth face constituting inner surfaces on a bottom wall portion side of said wall portions disposed at both sides of said bottom wall portion, and
said third face provided on an upstream side in said rotational direction of said rotor is formed with a fifth surface slanted toward said bottom wall portion and formed by cutting out an opening side of said concave space.

8. The air-driven rotary cutting tool as set forth claim 7, wherein an area where said second air channel is provided is, with respect to a circumferential direction around said rotary axis, larger than an area where said air supply port is provided.

9. The air-driven rotary cutting tool as set forth in claim 8, wherein said area where said second air channel is provided is, with respect to a circumferential direction around said rotary axis, formed in an entire peripheral area of said circumferential direction of said rotary axis except for an area close to said exhaust port.

10. The air-driven rotary cutting tool as set forth in claim 7, wherein:
there are a plurality of second air channels, and an area where said second air channels are provided is divided into a plurality of areas, and
each first face of that is included in each of said plurality of areas is disposed at a different angle with respect to a radial direction of said rotary axis.

11. The air-driven rotary cutting tool as set forth in claim 10, wherein a tangential angle formed between a center line of said first face included in said each of said plurality of areas and a tangential line where the center line crosses an inner circumference of said hollow portion becomes smaller toward said downstream side in said rotational direction of said rotor.

12. The air-driven rotary cutting tool as set forth in claim 11, wherein:
said rotor has a ring-like hub comprising two ring portions which are of different diameters and concentric therewith; and
said first turbine blade portion is provided on an outer circumference of one of said two ring portions, while said second turbine blade portion is provided on an outer circumference of another one of said two ring portions, said one of said two ring portions being greater in diameter than said another one of said two ring portions.

* * * * *